United States Patent [19]

Hawkins et al.

[11] Patent Number: 4,656,043
[45] Date of Patent: Apr. 7, 1987

[54] PEROXIDE-CONTAINING CONDITIONING SHAMPOO

[75] Inventors: Geoffrey R. Hawkins, Cheshire; Oksana A. Kowcz, Monroe, both of Conn.

[73] Assignee: Richardson-Vicks Inc., Wilton, Conn.

[21] Appl. No.: 775,682

[22] Filed: Sep. 13, 1985

[51] Int. Cl.[4] .......................... A61K 7/06; A61K 7/42; A61K 7/44
[52] U.S. Cl. ...................................... 424/70; 424/59; 424/60
[58] Field of Search .............................. 424/70, 71, 72

[56] References Cited

U.S. PATENT DOCUMENTS 3,378,444  4/1968  Swanson ................................ 424/62
3,488,287  1/1970  Seglin et al. ...................... 424/73 X
3,639,574  2/1972  Schmolka ........................ 424/62 X

FOREIGN PATENT DOCUMENTS 1083007  9/1967  United Kingdom ................... 424/62
2057261  4/1981  United Kingdom ................... 424/70
2068031  8/1981  United Kingdom ................... 424/71
2114616  8/1983  United Kingdom ................... 424/72

OTHER PUBLICATIONS

Kogyo, Chem. Abs., 1983, vol. 98, p. 162826z.
Van den Brom, Chem. Abs., 1979, vol. 94, p. 86123t.
Lemetre et al, Chem. Abs., 1971, vol. 74, p. 57209g.

Primary Examiner—Dale R. Ore
Attorney, Agent, or Firm—Salvatore R. Conte

[57] ABSTRACT

A stable aqueous hair conditioning shampoo composition comprising an aqueous solution of hydrogen peroxide, a specific anionic surfactant, at least one nonionic surfactant, an acidic pH-producing agent and one or more hair conditioning components.

4 Claims, No Drawings

PEROXIDE-CONTAINING CONDITIONING SHAMPOO

FIELD OF THE INVENTION

The invention relates to a hair conditioning shampoo composition especially suitable for treating permanently waved hair.

BACKGROUND OF THE INVENTION

Permanent waving is a process whereby a reducing agent is applied to the hair structure to open the disulfide linkages of the hair which are formed by the amino acid cystine. In the conventional two-step perming process, hair is wound onto an appropriate mandrel, e.g., roller or rod, etc., prior to and/or following reduction with a suitable reducing agent. The protein chains flow under tension to assume the imparted shape. After rinsing, an oxidizing agent (also termed a neutralizer) such as hydrogen peroxide is then applied, generally at ambient or elevated temperatures, to re-establish or close the disulfide linkages of the hair which, in effect, hardens the protein structure to set the hair in conformity with the shape of the mandrel. Excess oxidizing agent is then rinsed from the hair and the hair dried.

To date it has not been accepted cosmetic practice to shampoo and/or condition hair which has been newly permed since, as a general rule, commercially available shampoo/conditioner formulations adversely affect the setting or curl retention features of the permed hair. This is believed due to the fact that deposition of shampooing and/or conditioning materials on the permed hair would inhibit the naturally occurring air oxidation (neutralization) process which is desirable to further the closing of those disulfide linkages which may have remained open after the perming process.

In contrast, the hair conditioning shampoo composition of this invention provides a shampooing and conditioning treatment for permed hair without adversely affecting the permed condition of the hair. Indeed, the subject compositions, which may be advantageously used even immediately after perming, furthers the curl retention feature of the permed hair, thereby extending the life of the laid permanent wave.

DETAILED DESCRIPTION OF THE INVENTION

The hair conditioning shampoo composition herein provided comprises an aqueous solution of hydrogen peroxide, a specific anionic surfactant, at least one nonionic surfactant, an acidic pH-producing agent and one or more hair conditioning components. More specifically, the invention provides a stable, aqueous hair conditioning shampoo composition containing from about 2 to about 2.5 percent of active hydrogen peroxide, at least about 3 percent by weight of sodium lauryl ether sulfate (SLES) as the sole anionic surfactant, at least about 5 percent by weight of a nonionic surfactant component, a sufficient amount of an acid component to provide the composition with a pH of from about 3 to about 4, and an effective hair conditioning amount of a hair conditioning component compatible with hydrogen peroxide.

Said ingredients provide a formulation suitable for use on permed hair which is very effective with regard to lathering and cleansing and which also effectively conditions as it cleans, that is, the hair becomes more manageable, whereby the combability of the hair is markedly improved, the hair appears to have more body and the hair exhibits improved luster. In addition to these benefits, the low pH/peroxide profile of the formulation enhances the neutralization step of the perming process by helping to firmly lock those disulfide linkages which may not have been closed due to insufficient or uneven neutralization, a frequent cause of perm failure, thereby assuring long-lasting bouncy curls.

As set forth above, the composition of the invention comprises a stable aqueous formulation containing the five indicated essential components, other than water, all of which are preferably present in about the following ranges:

| | |
|---|---|
| 1. Active hydrogen peroxide | 2–2.5% |
| 2. Sodium lauryl ether sulfate | 3–40% w/w |
| 3. Nonionic surfactant | 5–20% w/w |
| 4. Acid, sufficient to provide pH | 3–4 |
| 5. Hair conditioner | 1–10% w/w |
| 6. Water, q.s. ad | 100% |

Hydrogen peroxide is readily available in aqueous solution form from various commercial entities, for example, as 35%, 50%, 70% solutions from DuPont under its trademark "Albone". The term "active hydrogen peroxide" relates to the availability of hydrogen peroxide as determined by standard assay procedures, such as, for example, the standard "Assay of Hydrogen Peroxide Solutions" issued by the Cosmetic, Toiletry and Fragrance Association, Inc. (CTFA) on Oct. 15, 1974 as CTFA Method E29-1; and the standard "Stability of Hydrogen Peroxide Solutions" assay issued by the CTFA on Oct. 15, 1974 as CTFA Method E30-1. In accordance with this invention, the subject compositions have from about 2 to about 2.5 percent active hydrogen peroxide when subjected to both the aforementioned CTFA assay procedures.

The anionic component, sodium lauryl ether sulfate (SLES), is also known by its CTFA adopted name as sodium laureth sulfate and is also readily available from diverse commercial sources.

Any nonionic surface active agent known to be useful in the formulation of hair shampoo compositions may be likewise used in the compositions of this invention. Among the various nonionic surfactants there may for instance be mentioned nonylphenolpolyglycol ethers, sorbitan fatty acid esters, fatty acid ethoxylates and fatty alcohol ethoxylates. Typical ethoxylated nonionic surfactants include ethoxylated mono and polyhydric alcohols having 10 to 18 carbon atoms and more than 5 moles of ethoxylation; ethoxylated alkylphenols having 6 to 12 carbon atoms in the alkyl group and 5 to 200 moles of ethoxylation; ethoxylated fatty acids having 10 to 18 carbon atoms and 5 to 200 moles of ethoxylation; ethoxylated lanolin derivatives; and ethoxylated sorbitans, including fatty acid esters of sorbitol having 10 to 18 carbon atoms and ethoxylated with 10 to 200 moles of ethylene oxide. Nonionic surfactants are readily available under many commercial brand names including the polyoxyalkylene derivatives of propylene glycol sold by BASF-Wyandotte Corp., Parsippany, NJ, under its "Pluronic" trademark; and the polyoxyethylene derivatives of fatty acid partial esters of sorbitol anhydrides sold by ICI United States, Inc., Wilmington, DE, under its "Tween" trademark. One or more nonionic surfactants may be utilized as the essential nonionic surfactant component of the subject compositions.

As the acid component there may be used an inorganic acid such as, for example, phosphoric, sulfuric, nitric and the like acids, or an organic acid such as, for example, citric, sorbic and the like acids. The choice of acid obviously must be one that does not decompose the essential hydrogen peroxide component, that is, it must be peroxide compatible. One or more such acids may be utilized as the essential acid component of the subject compositions.

With regard to the essential hair conditioning component, it is known to add to shampoos small amounts of compounds, customarily called conditoners, which are intended to advantageously effect (i.e., condition) some cosmetic parameter of the treated hair, for example, lustre, manageability, feel, texture, combability, body and the like, by depositing such compounds on the hair during use. One or more such compounds may be utilized herein as the hair conditioning component provided that the particular compound employed is stable at the composition pH and peroxide compatible, that is, it does not adversely affect the stability of the hydrogen peroxide in the subject composition. In this regard, for example, it is well known that metals, particularly heavy metals, will decompose hydrogen peroxide to render it inactive. Accordingly, a hair conditioning compound containing such a metallic ion is to be avoided.

Apart from various other compounds used for conditioning purposes, there are frequently used quaternary ammonium compounds and ethoxylated alkylolamides. Preferred conditioning compounds which may be utilized in the subject composition include, for example, cationic conditioners such as polyquaternium-7, polyquaternium-10, steartrimonium hydrolyzed animal protein, cocamidopropylamine oxide, cocamidopropyl betaine and the like (the latter two conditioners being cationic at the subject composition's pH 3-4), and non-cationic conditioners such as panthenyl ether ether, panthenol, phytantriol, dimethicone copolyol, polysorbate-20, PEG-75 lanolin and the like.

The conditioning shampoo of the invention may contain one or more optional ingredients customarily used for conventional shampoo compositions such as, for example, preservatives, dyes and other colorants, odorants and odor counteractants, U.V.-absorbers, viscosity adjusting agents, dandruff removers, protein hydrolysates and other protein derivatives, foam boosters, lanolin compounds and the like, said ingredients being compatible with peroxide.

The invention will now be further illustrated by, but not intended to be limited by, the following examples.

EXAMPLE 1

A stable aqueous hair conditioning shampoo with pH about 3.7 is provided from:

| Ingredients | |
| --- | --- |
| SLES | 6.00% w/w |
| Cocamidopropylamine oxide | 1.00% w/w |
| Polysorbate 20 | 8.00% w/w |
| Citric acid, hydrous, sufficient | to pH 3.7 |
| Hydrogen peroxide (35%) | 5.71% w/w |
| Distilled water, q.s. ad | 100.00% w/w |

The first three ingredients are added one at a time with stirring to about 75% w/w of the distilled water at ambient temperature until thoroughly mixed. Enough citric acid is added to provide pH about 3.7. The hydrogen peroxide is mixed in and distilled water added to 100% w/w. Permed hair shampooed with this composition within one hour demonstrates substantially increased curl retention as compared to permed hair subsequently shampooed with "Sassoon Normal Shampoo", a commercially available shampoo from Vidal Sassoon, Inc., Los Angeles, CA.

EXAMPLE 2

This example illustrates best mode compositions of this invention containing additional optional ingredients. Each ingredient is identified by its generic chemical name or by its CTFA (Cosmetic, Toiletry and Fragrance Association, Inc.) adopted name.

| | | % w/w | |
| --- | --- | --- | --- |
| | Ingredients | A | B |
| 1. | Distilled water | 74.034 | 68.679 |
| 2. | Citric acid, hydrous (pH agent) | 0.800 | 0.450 |
| 3. | Zinc citrate (odor counteractant) | 0.100 | — |
| 4. | Polyquaternium-10 (cationic conditioner) | 0.200 | 0.100 |
| 5. | PEG-120 methyl glucose dioleate (thickener) | 5.800 | 5.800 |
| 6. | Cocamidopropylamine oxide (conditioning surfactant) | 0.500 | 1.000 |
| 7. | SLES (anionic surfactant) | 3.000 | 6.000 |
| 8. | Cocamide DEA (conditioning surfactant) | 1.000 | 3.000 |
| 9. | Polysorbate 20 (nonionic surfactant) | 6.000 | 6.000 |
| 10. | Octyl dimethyl PABA (U.V. absorber) | 0.100 | 0.050 |
| 11. | Phytantriol (conditioner) | 0.001 | 0.001 |
| 12. | Panthenyl ethyl ether (conditioner) | 0.010 | 0.010 |
| 13. | Steartrimonium hydrolyzed animal protein (cationic conditioner) | 0.100 | 0.100 |
| 14. | Panthenol (conditioner) | 0.100 | 0.100 |
| 15. | Polysorbate 20 (nonionic surfactant) | 2.000 | 2.000 |
| 16. | Peroxide compatible odorant | 0.500 | 1.000 |
| 17. | PEG-40 castor oil & guaiazulene (colorant) | 0.025 | — |
| 18. | 1% solution FD&C blue #1 (colorant) | 0.020 | — |
| 19. | Hydrogen peroxide (35%) | 5.710 | 5.710 |
| | | 100.000 | 100.000 |

Heat ingredient #1 to 75° C., and then add ingredients #2 through 9, with stirring at moderate speed making sure each ingredient is completely in solution before the next addition. Premix ingredients #10 and #11, heat to 65° C. and add to the batch with stirring. Cool batch to 50° C. and then add ingredients #12 through #14 with stirring. Premix ingredients #15 and #16 and stir into batch at 45° C. Add ingredients #17 and #18 (for composition A) with stirring when batch temperature is at 40° C. Cool batch to 30° C. and mix in ingredient #19. The pH of composition A is about 3.30 and of composition B of about 3.85.

EXAMPLE 3

Improved Curl Efficacy

Virgin hair swatches, approximately 2 grams in weight, are bound together at one end and trimmed to 7 inches. After spraying with water to moisten, the hair swatch is wound tightly around a 1 cm diameter perming rod and then permed with one of the following two commercially available permanent waving solutions: "Pantene Professional Vitamin Exothermic Self-Timing Wave" (an alkaline wave) and "Perfect Transition Vitamin Exothermic Acid-Balanced Wave" (an acid wave), both from The Pantene Company, Division of Richardson-Vicks Inc., Wilton, CT. The moistened hair swatch is permed in the respective waving solution, 15 minutes with the former and 20 minutes with the latter, and then thoroughly rinsed with water. For each permanent waving solution, one swatch is left unneutralized (Sample A); one is neutralized with the particular neutralizer provided with the respective commercial product (Sample B); one is similarly neutralized and shampooed once with the hair conditioning shampoo of Example 2-A (Sample C); one is not neutralized but shampooed twice with said shampoo (Example D); and, finally, one is not neutralized but shampooed twice with a commercially available shampoo, "Vidal Sassoon Original Salon Formula Shampoo" from Vidal Sassoon, Inc., Los Angeles, CA (Example E). After neutralization, the swatch is removed carefully from the perming rod, treated with the particular shampoo as indicated, rinsed thoroughly with water, towel-blotted dry, and then recurled onto a 1.5 cm diameter roller. Each rolled hair swatch is then dried under a standard salon hair dryer until dry. After drying, the hair swatch is carefully unwound from the roller and hung vertically from the bound end. The swatch is then combed through once. The initial length of the curl is measured before exposure in the humidity chamber and this measurement serves as the control basis against which the curl efficiency measured as percent droop, i.e., percent loss in curl retention, is determined. The hair swatches are placed in a humidity chamber set at 90% relative humidity (RH) and 37° C. Relaxation of the swatches is measured periodically in the humidity chamber. The lesser the percent droop, the more effective is the prescribed treatment. The percent droop, or percent loss in curl retention, is determined by the formula:

$$\% \text{ Droop} = \frac{\text{length at given humidity for given time} - \text{initial length}}{\text{initial length}} \times 100$$

As indicated by the following tabulated data, The results obtained with the hair conditioning shampoo of Example 2-A consistently provide lower percent droop values, thereby indicating better curl retention than non-peroxide containing shampoos. The measurements of percent droop are recorded the same day as the swatches are permed ("I") and again 24 hours later ("24"). Similarly beneficial results in curl retention are obtainable with the hair conditioning shampoo of Example 2-B.

TABLE I

| Sample | Alkaline Wave | | | |
|---|---|---|---|---|
| | 10 Mins. | 20 Mins. | 30 Mins. | 45 Mins. |
| A | I - 334% | I - 400% | I - 434% | I - 467% |
| | 24 - 334% | 24 - 467% | 24 - 500% | 24 - 500% |
| B | I - 167% | I - 247% | I - 267% | I - 300% |
| | 24 - 200% | 24 - 500% | 24 - 500% | 24 - 500% |
| C | I - 20% | I - 200% | I - 420% | I - 500% |
| | 24 - 134% | 24 - 300% | 24 - 300% | 24 - 367% |
| D | I - 20% | I - 200% | I - 420% | I - 500% |
| | 24 - 134% | 24 - 300% | 24 - 300% | 24 - 367% |
| E | I - 480% | I - 650% | I - 650% | I - 720% |
| | 24 - 433% | 24 - 534% | 24 - 567% | 24 - 567% |

TABLE II

| Sample | Acid Wave | | | |
|---|---|---|---|---|
| | 10 Mins. | 20 Mins. | 30 Mins. | 45 Mins. |
| A | I - 317% | I - 567% | I - 567% | I - 650% |
| | 24 - 334% | 24 - 534% | 24 - 534% | 24 - 567% |
| B | I - 167% | I - 267% | I - 300% | I - 300% |
| | 24 - 267% | 24 - 467% | 24 - 467% | 24 - 500% |
| C | I - 150% | I - 275% | I - 317% | I - 317% |
| | 24 - 234% | 24 - 400% | 24 - 400% | 24 - 400% |
| D | I - 275% | I - 358% | I - 400% | I - 484% |
| | 24 - 200% | 24 - 367% | 24 - 400% | 24 - 400% |
| E | I - 300% | I - 400% | I - 467% | I - 500% |
| | 24 - 334% | 24 - 534% | 24 - 534% | 24 - 534% |

EXAMPLE 4 improved Curl Efficacy

Following the procedure of Example 3, a further comparison with both the alkaline and acid permanent waving solutions utilized therein is provided wherein one swatch of permed hair is neutralized with the particular neutralizer provided with the respective commercial product (Sample F); another swatch is similarly neutralized and shampooed once with the hair conditioning shampoo of Example 2-A (Sample G); and, finally, an additional swatch is similarly neutralized and shampooed twice with the commercially available shampoo identified in Example 3 (Sample H).

TABLE III

| Sample | Alkaline Wave | | | |
|---|---|---|---|---|
| | 10 Mins. | 30 Mins. | 45 Mins. | 60 Mins. |
| F | I - 167% | I - 400% | I - 433% | I - 467% |
| G | I - 186% | I - 436% | I - 436% | I - 472% |
| H | I - 200% | I - 500% | I - 750% | I - 750% |

TABLE IV

| Sample | Acid Wave | | | |
|---|---|---|---|---|
| | 10 Mins. | 30 Mins. | 45 Mins. | 60 Mins. |
| F | I - 300% | I - 600% | I - 650% | I - 650% |
| G | I - 100% | I - 233% | I - 267% | I - 300% |
| H | I - 233% | I - 400% | I - 400% | I - 434% |

We claim:

1. A stable aqueous hair conditioning shampoo composition comprising from about 2 to about 2.5 percent of active hydrogen peroxide, at least about 3 percent by weight of sodium lauryl ether sulfate as the sole anionic surfactant, at least about 5 percent by weight of a nonionic surfactant component, a sufficient amount of an acid component to provide the composition with a pH of from about 3 to about 4, and an effective hair conditioning amount of a hair conditioning component, said acid component and said conditioning component being compatible with said peroxide.

2. A stable aqueous hair conditioning shampoo composition comprising from about 2 to about 2.5 percent of active hydrogen peroxide, from about 3 to about 40 percent by weight of sodium lauryl ether sulfate, from about 5 to about 20 percent by weight of a nonionic surfactant component, a sufficient amount of an acid component to provide the composition with a pH of from about 3 to about 4, and from about 1 to about 10 percent by weight of a hair conditioning component, said acid component and said conditioning component being compatible with said peroxide.

3. A stable aqueous hair conditioning shampoo composition consisting essentially of the following ingredients in about the indicated amounts:

| Ingredients | % w/w |
| --- | --- |
| Distilled water | 74.034 |
| Citric acid, hydrous | 0.800 |
| Zinc citrate | 0.100 |
| Polyquaternium-10 | 0.200 |
| PEG 120 methyl glucose dioleate | 5.800 |
| Cocamidopropylamine oxide | 0.500 |
| Sodium lauryl ether sulfate | 3.000 |
| Cocamide DEA | 1.000 |
| Polysorbate 20 | 8.000 |
| Octyl dimethyl PABA | 0.100 |
| Phytantriol | 0.001 |
| Panthenyl ethyl ether | 0.010 |
| Steartrimonium hydrolyzed animal protein | 0.100 |
| Panthenol | 0.100 |
| Peroxide compatible odorant | 0.500 |
| PEG 40 castor oil & guaiazulene | 0.025 |
| 1% solution FD&C blue #1 | 0.020 |
| Hydrogen peroxide (35%) | 5.710 |
| | 100.000. |

4. A stable aqueous hair conditioning shampoo composition consisting essentially of the following ingredients in about the indicated amounts:

| Ingredients | % w/w |
| --- | --- |
| Distilled water | 68.679 |
| Citric acid, hydrous | 0.450 |
| Polyquaternium-10 | 0.100 |
| PEG 120 methyl glucose dioleate | 5.800 |
| Cocamidopropylamine oxide | 1.000 |
| Sodium lauryl ether sulfate | 6.000 |
| Cocamide DEA | 3.000 |
| Polysorbate 20 | 8.000 |
| Octyl dimethyl PABA | 0.050 |
| Phytantriol | 0.001 |
| Panthenyl ethyl ether | 0.010 |
| Steartrimonium hydrolyzed animal protein | 0.100 |
| Panthenol | 0.100 |
| Peroxide compatible odorant | 1.000 |
| Hydrogen peroxide (35%) | 5.710 |
| | 100.000. |

* * * * *